US007044127B1

(12) United States Patent
Fernandez DeCastro

(10) Patent No.: US 7,044,127 B1
(45) Date of Patent: May 16, 2006

(54) MULTIPURPOSE MASK

(76) Inventor: Aurora L. Fernandez DeCastro, P.O. Box 1984, Elkhart, IN (US) 46515

(*) Notice: Subject to any disclaimer, the term of this patent is extended or adjusted under 35 U.S.C. 154(b) by 0 days.

(21) Appl. No.: 10/659,325

(22) Filed: Sep. 11, 2003

(51) Int. Cl.
*A61M 15/00* (2006.01)

(52) U.S. Cl. ........................... 128/202.15; 128/205.27; 128/206.12; 128/206.19

(58) Field of Classification Search ........... 128/201.22, 128/201.23, 206.12, 206.17, 206.18, 206.19, 128/206.21, 206.28, 207.11, 206.22, 202.15, 128/206.16, 206.29, 201.25, 201.29, 202.16, 128/205.25, 205.27; 2/6.1, 205
See application file for complete search history.

(56) References Cited

U.S. PATENT DOCUMENTS 2,023,267 A * 12/1935 de Saint-Rapt et al. . 128/202.15
3,067,425 A * 12/1962 Colley ............................ 2/6.2
3,731,717 A * 5/1973 Potash ........................ 141/379
4,084,585 A 4/1978 Venaleck
4,185,329 A * 1/1980 Sarazen ............................. 2/8
4,328,797 A * 5/1982 Rollins et al. ......... 128/202.27
4,424,833 A * 1/1984 Spector et al. .............. 137/849
4,433,684 A * 2/1984 Sarnoff et al. ......... 128/203.21
4,626,245 A * 12/1986 Weinstein .............. 604/167.04
4,823,785 A * 4/1989 Mancosu et al. ...... 128/202.15
4,841,963 A * 6/1989 Vandeputte ............ 128/202.15
4,890,609 A * 1/1990 Wilson, II ............. 128/206.29
4,961,420 A * 10/1990 Cappa et al. .......... 128/207.12
5,007,421 A * 4/1991 Stewart ................. 128/204.18
5,701,892 A 12/1997 Bledstein
5,717,991 A 2/1998 Nozaki et al.
6,095,143 A 8/2000 Dyrud et al.
6,098,201 A 8/2000 Boros, Sr.
6,123,077 A 9/2000 Bostock et al.
6,610,031 B1 * 8/2003 Chin ..................... 604/167.04
6,615,829 B1 * 9/2003 Horn et al. ............ 128/202.15
6,691,703 B1 * 2/2004 McKinney et al. .... 128/203.11
6,718,971 B1 * 4/2004 Horn et al. ............ 128/202.15
6,758,215 B1 * 7/2004 Begum .................. 128/203.29

FOREIGN PATENT DOCUMENTS

WO WO 99/27999 A1 * 6/1999

* cited by examiner

*Primary Examiner*—Aaron J. Lewis
(74) *Attorney, Agent, or Firm*—Browdy and Neimark, PLLC

(57) ABSTRACT

A protective, multipurpose mask covers the oral and nasal areas. The mask has an opening about or around the mouth area of the wearer which allows different devices to be inserted and withdrawn from the wearer's mouth while the mask is in place on the wearer.

9 Claims, 5 Drawing Sheets

MULTIPURPOSE MASK

FIELD OF THE INVENTION

The present invention relates to a mask that protects the mouth and nose but which provides a closable opening so that the wearer is able to eat or drink without having to remove the mask. This multipurpose mask allows for insertion of devices through the mask while the mask is on.

BACKGROUND OF THE INVENTION

Filtration respirators, or face masks, have been widely used in the past to protect the respiratory system from particulate or chemical agents. These masks are designed to minimize the transmission of contagious diseases or to protect the respiratory system from toxic substances or allergens in the surrounding atmosphere.

Protective face masks are generally used for preventing the transmission of contagious diseases, as well as to protect from inhalation of industrial or city dust or dirt, chemicals, allergens, and the like that may be present in the atmosphere. These masks are used to maintain a private, enclosed space around the breathing orifices when a person is in close proximity to other persons, or if an undesirable atmospheric agent is present. Additionally, infectious persons can wear masks to protect other people in the vicinity from their pathogens.

A variety of masks have been proposed which have different features, such as different ways of retaining the mask in place, providing different degrees of comfort for the wearer, having inhaling or exhausting valves, different types of seals around the mask for tighter sealing of the mask to the wearer's face. Other features include impregnating the mask with certain chemicals to make the mask more effective against air borne substances, and sterilizing the mask to enhance its cleanliness.

However, when the wearer wishes to eat or drink, all of the above masks must be removed so that food or drink can be imbibed. Of course, removing the mask means that the face is no longer protected.

Examples of some of these types of masks can be found in U.S. Pat. No. 2,494,406, which shows a protective mask which has elastic temple straps attached to the mask to enhance the conforming to the face of the wearer.

U.S. Pat. No. 6,098,201 shows a molded face mask made of a plastic sheet in which a deformable wire is embedded so that the mask better conforms to the wearer's face.

U.S. Pat. No. 4,827,923 shows a protective facial mask that slips over the user's head.

U.S. Pat. No. 6,123,077 discloses a mask with a flat central panel to which other panels are joined through a fold line, seam, weld, or bond.

U.S. Pat. No. 4,974,586 shows a breathing mask which comprises an inhalation valve disposed in an opening of the wall of the mask. The inhalation valve opens at a sufficiently low breathing pressure to make it comfortable.

U.S. Pat. No. 5,699,792 shows a face mask with an enhanced facial seal.

U.S. Pat. No. 5,701,892 shows a two-sided chamber held away from the entrance of the nostrils and the mouth by a rigid support.

U.S. Pat. No. 4,941,470 shows a face mask having pleats formed therein and a method for fabricating the mask.

U.S. Pat. No. 6,394,090 shows a respiratory device having first and second lines of demarcation bisected by a fold so that the device can be folded.

U.S. Pat. No. 4,856,509 discloses a face mask containing a chemical or biological agent that destroys microorganisms such as viruses and bacteria.

U.S. Pat. No. 5,819,731 shows a face mask having a combination of adjustable ear loops and drop down band for a snug fit.

U.S. Pat. No. 5,717,991 shows a disposable sanitary mask comprising a cover panel section adapted to cover the wearer's nose and mouth and a pair of ear loops and panel sections to prevent the mask from losing its shape.

U.S. Pat. No. 5,735,270 discloses a disposable foldable face mask with face seal characteristics for a high efficiency filtering medium.

U.S. Pat. No. 6,213,125, disclose a device for protecting the face of the wearer including a gas pervious mask dimensioned to fit over the nose and mouth and a shield to protect the eyes of the wearer.

U.S. Pat. No. 6,332,465 discloses face masks having elastic polyolefin thermoplastic bands attached thereto by heat and pressure.

U.S. Pat. No. 6,055,982 discloses a face mask which prevents transmission of air borne aerosols, particulate matter, and/or liquids, having an enhanced fluid barrier between the periphery of the mask and the wearer's face.

However, in all of these masks, when the wearer wishes to eat or drink, the mask must be removed, subjecting the wearer to the very allergens, chemicals, etc. from which the mask is worn to protect the wearer.

SUMMARY OF THE INVENTION

It is an object of the present invention to overcome the aforesaid deficiencies in the prior art.

It is another object of the present invention to provide a protective mask that need not be removed when the wearer wishes to eat or drink.

It is a further object of the present invention to provide a multipurpose mask that allows the wearer to insert devices into the mouth without removing the mask.

It is yet another object of the present invention to maintain some protection from the environment even when the wearer requires hydration or nutrients.

It is still another object of the present invention to provide a unique mask that can allow insertion through the mask of different devices that may be needed at different times.

It is another object of the present invention to provide a mask that can be worn by the user for extended periods of time that are not limited to times not needed for sustenance of the wearer.

It is a further object of the present invention to provide a simple and economical mask that protects the wearer from impurities and irritants in the surrounding atmosphere at all times.

The mask of the present invention is uniquely designed to have at least one opening or area that can be opened so that the wearer can take nourishment or insert needed devices, such as an oxygen tube, without removing the mask. This opening or area is located near the mouth of the wearer to make nourishment accessible, preferably within a short distance from the mouth.

The area designed for introduction of nourishment is readily re-closed after nourishment is taken, or the device is removed, thus providing the greatest degree of protection for the wearer. This area can be a hole which can be closed by a flap when not needed, or closed by a totally detachable patch. Alternatively, the area can be a closed area that permits a delivering device, such as a straw, spoon or tube, to be inserted, and which self closes or self reseals once the wearer no longer needs the device.

The mask of the present invention has a multiplicity of functions, while being economical to manufacture. The device can be used in airplanes, dance studios, subways, offices, schools, hospitals, post offices, governmental offices, shopping centers, homes or any other place where protection is needed without sacrificing hydration or sustenance for the wearer.

At times such as the present, in which dangerous health risks can be present anywhere in the surrounding atmosphere, the present invention provides protection from the environment even when the wearer needs hydration or nutrition.

The masks can be packaged individually and dispensed from vending machines.

BRIEF DESCRIPTION OF THE DRAWINGS

FIG. 5*a* is a schematic diagram of a detachable cover for use on the mask shown in FIG. 5.

DETAILED DESCRIPTION OF THE INVENTION

Figure 1:
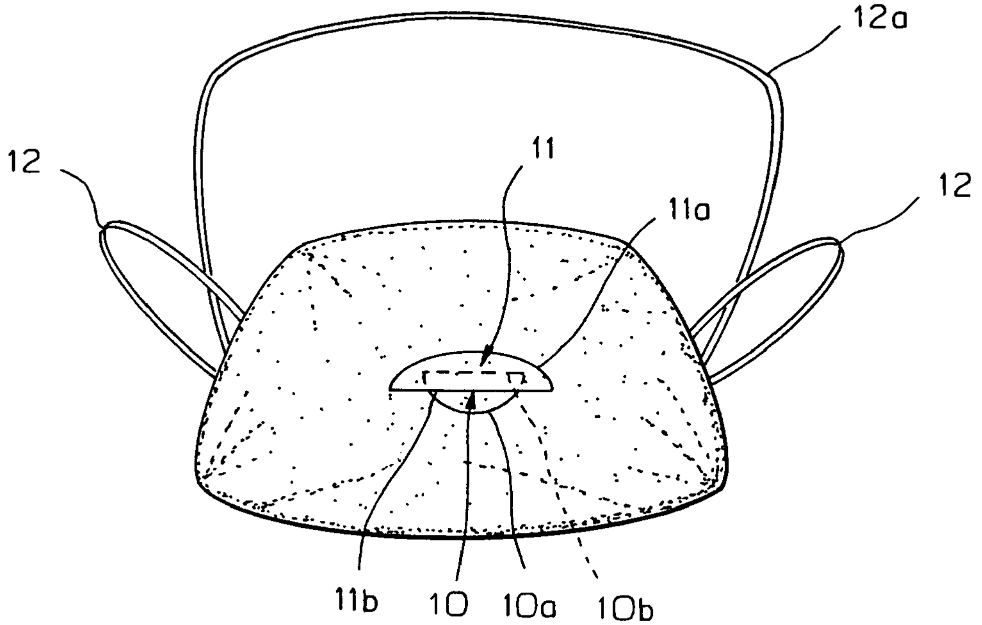
FIG. 1 is a schematic front view of one embodiment of a mask according to the present invention.

FIG. 1 shows one embodiment of a mask according to the present invention. The mask is made of any type of material that can be comfortably worn, either flexible or inflexible. In the area approximately covering the mouth of a wearer, a piece of flexible, elastic material 10 is attached to the mask indicated by 10*a* except for an area which approximately covers the lower lip of the wearer indicated by 10*b*, which is free. This elastic or flexible material is also used to form a separate cover for the upper or high lip of the wearer 11. The high lip 11 is attached to the mask indicated by 11*a* except for the lower edge of the high lip 11*b*. The free edge 11*b* of the high lip extends over the free edge of the low lip 10*b*.

The mask may be retained in place on the wearer by a variety of means, including loops over the ears 12, or an elastic band 12*a* stretching across the back of the wearer's head.

Figure 2:
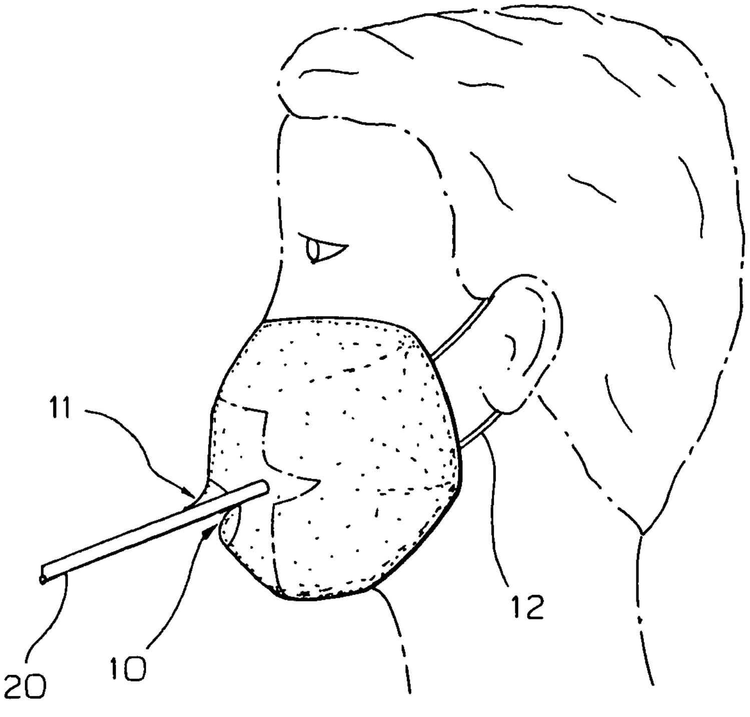
FIG. 2 is a schematic side view of the mask of FIG. 1.

FIG. 2 shows a side view of the mask of FIG. 1 in place on a wearer. Bands 12 hold the mask in place on the wearer by encircling the ears of the wearer. The opening provided in the mask to permit the wearer to eat or drink without the necessity for removing the mask is shown with a device 20 inserted between the high lip 11 and the low lip 10 in the mouth of the wearer.

Figure 3:
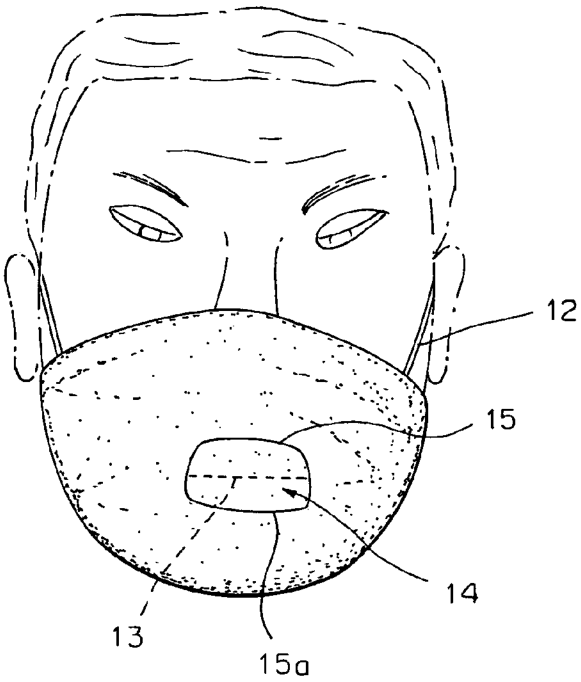
FIG. 3 is a schematic front view of another mask with attachments to keep it in place.
Figure 3A:
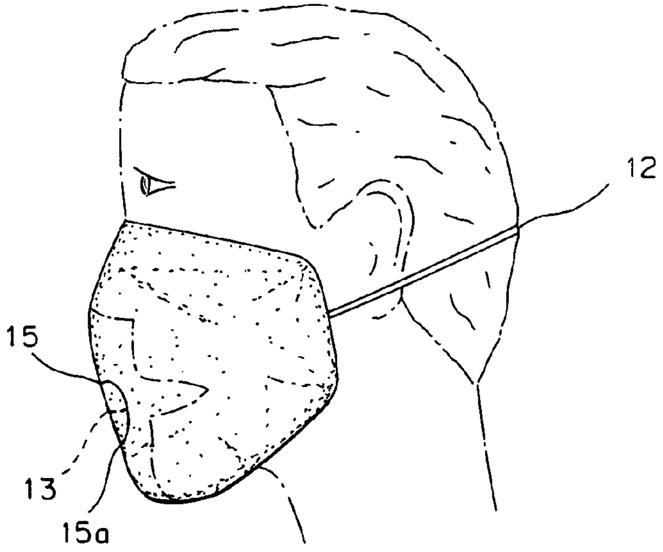
FIG. 3*a* shows a schematic side view of the multipurpose mask of FIG. 3

Another embodiment of a mask according to the present invention is shown in FIG. 3. This mask has an aperture 13 in approximately the location of the wearer's mouth, which aperture 13 is covered by a flap 14 attached to the mask above the aperture indicated by 15. The lower part of the flap 15*a* is lightly attached to the mask so that the flap 14 can be raised when the wearer chooses to ingest food or beverages. FIG. 3*a* is a side view of the mask of FIG. 3 showing the solid flap 14 and the aperture 13 behind the flap 14 so that the wearer can insert a device through such aperture when the bottom of the flap 15*a* is raised.

Figure 4:
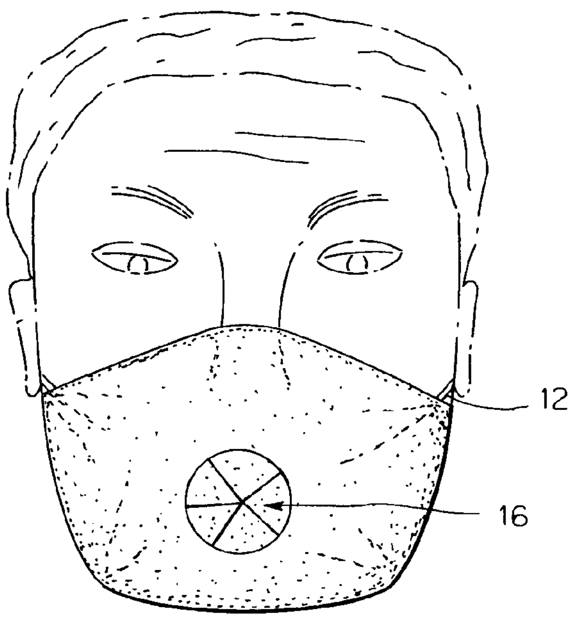
FIG. 4 shows a front view of yet another embodiment of a mask on a wearer.

FIG. 4 shows another embodiment of a mask according to the present invention having an area of elastic or flexible material 16 that is self-closing. That is, the flexible, or elastic self-closing area 16 is designed to close near the center of the flexible material.

Figure 4A:
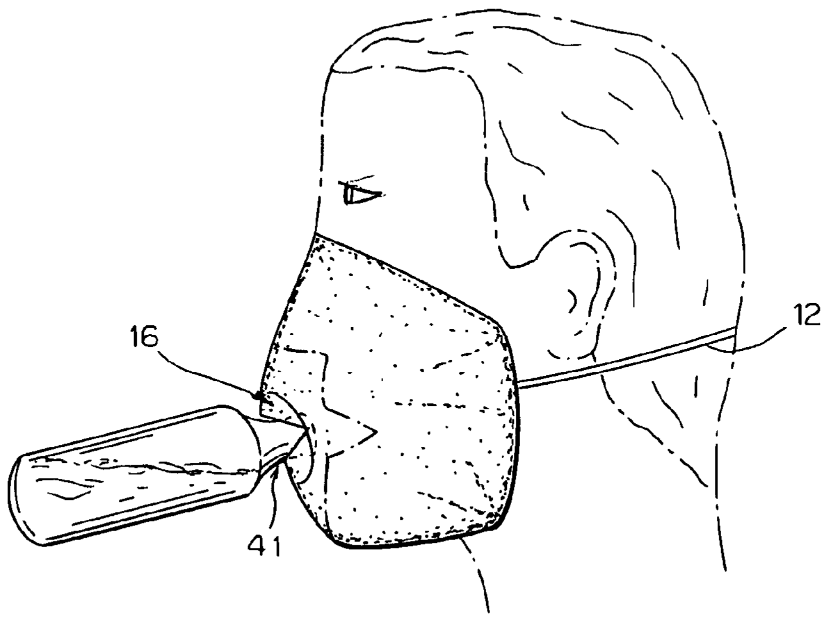
FIG. 4*a* is a schematic side view of FIG. 4 with a device inserted through the central point of the flexible area.

FIG. 4*a* illustrates how the flexible material 16 opens when, for example, a bottleneck 41 is inserted into the area of the flexible material 16 so that the wearer can ingest the contents of the bottle. Once the bottleneck 41 is removed, the flexible area 16 self-seals so that the mouth of the wearer is protected.

Figure 5:
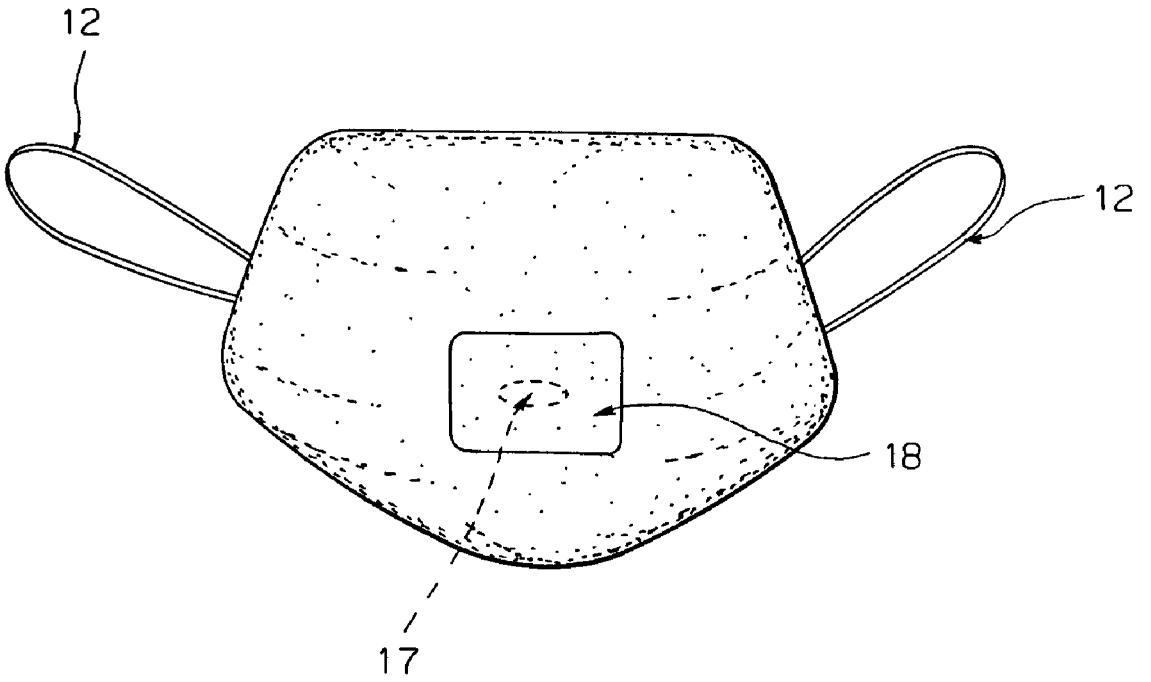
FIG. 5 shows another embodiment of a mask with a single aperture.

FIG. 5 shows a mask having a single orifice or aperture 17 through which the wearer can insert food or drink into the wearer's mouth. A detachable cover 18 covers the orifice when the wearer is not eating or drinking. This cover 18 can be attached to the mask by any conventional attaching or adhesive means, such as hook and loop closures, reusable adhesive, snaps, hooks and eyes, etc.

Figure 5A:
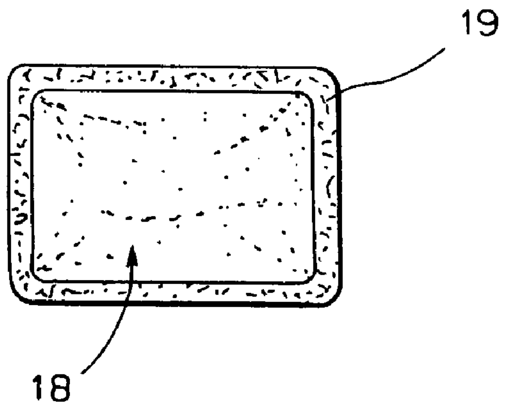
FIG. 5*a* shows the detachable cover for the mask.

FIG. 5*a* shows the detachable cover 18 with an adhesive 19 around the periphery of the cover.

While the mask has been shown for purposes of illustration as a face mask, the mask can be made in any configuration, such as a complete covering of the head.

Figure 6A:
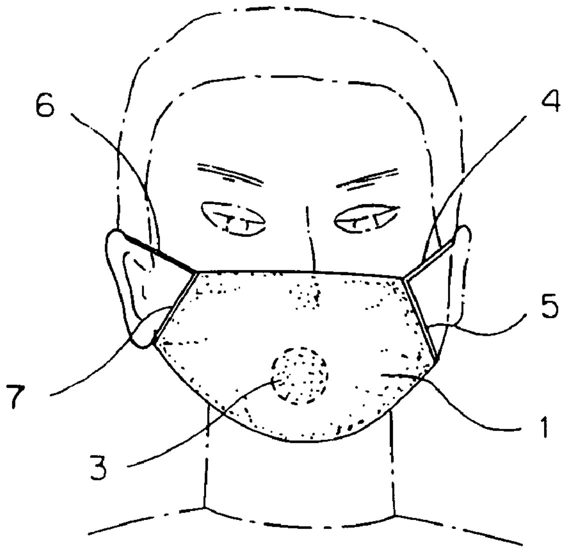
FIGS. 6A and 6B are schematic sketches of two types of multipurpose mask according to the present invention.
Figure 6B:
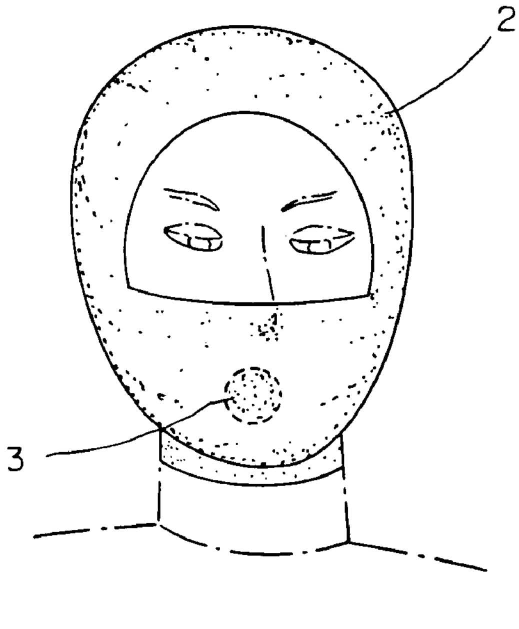

FIGS. 6A and 6B illustrate two different styles of masks according to the present invention. FIG. 6A shows a mask 1 which covers the lower half of the face of the wearer. Bands 4, 5, 6, and 7 hold the mask in place by encircling the ears of the wearer. An area 3 is provided for insertion and withdrawal of tubes, food, beverages, etc. FIG. 6B shows a mask 2 which covers the head of the wearer except for the eyes. An area 3 is provided for inserting and withdrawing foods, beverages, tubes, and the like.

At least part of the mask covering the mouth and nose of the wearer must comprise a filtering media in order to protect the wearer from airborne particulates, microorganisms, etc. The portions of the mask not formed of filtering media may be formed of a variety of materials, such as a material which provides a moisture barrier to prevent fogging of a wearer's glasses.

The filtering portion of the mask of the present invention, can be made of any acceptable material which will filter airborne pathogens or dust. Thus, the mask can be made of any of a number of woven or nonwoven materials, a single layer or a plurality of layers, with or without an inner or outer cover or scrim, and with or without a stiffening means or the mask can be molded. Examples of suitable filter material include microfiber webs, fibrillated film webs, woven or non-woven webs (e.g., airlaid or carded staple fibers), solution-blown fiber webs, or combinations thereof. Fibers useful for forming such webs include, for example, polyolefins such as polypropylene, polyethylene, polybutylene, poly(4-methyl-1-pentene), and blends thereof; halogen substituted polyolefins such as those containing one or more chloroethylene units or tetrafluoroethylene units, and which may also contain acrylonitrile units; polyesters; polycarbonates; polyurethanes; rosin-wool; glass; cellulose or combinations thereof.

Fibers of the filtering material are selected depending on the type of particulate to be filtered. Proper selection of fibers can also affect the comfort to the wearer, which is of great importance when the mask is to be worn for an extended period of time, such as on a long flight. Fibers can be selected to provide softness or moisture control, for example. Webs of melt blown fibers can be prepared as described, for example, in Wente, *Industrial Engineering Chemistry* 48, 1342 et seq. (1956). Blown microfibers used in masks according to the present invention preferably have an effective diameter of from about 3 to about 30 microns, more preferably from about 7 to 15 microns.

Staple fibers may also, optionally, be present in the mask. The presence of crimped, bulking staple fibers provides for a more lofty, less dense web than a web consisting solely of blown microfibers. Preferably, no more than 90 weight percent should be staple fibers, and more preferably, no more than 70 weight percent, of the filtering material should be staple fibers. Webs containing staple fibers are disclosed in Hauser, U.S. Pat. No. 4,118,531, the entire contents of which are hereby incorporated by reference.

The mask may also be made of bicomponent staple fibers.

In the mask embodiment in which the aperture is covered by a separate flap, the flap can be made of any type of material which is not irritating to the wearer. The flap may be of flexible, semi-rigid, or rigid material, although flexible material is preferred because it provides a closer fit over the aperture, thus better protecting the wearer's mouth.

The foregoing description of the specific embodiments will so fully reveal the general nature of the invention that other can, by applying current knowledge, readily modify and/or adapt for various application such specific embodiments without undue experimentation and without departing from the generic concept. Therefore, such adaptations and modifications should and are intended to be comprehended within the meaning and range of equivalents of the disclosed embodiments.

It is to be understood that the phraseology or terminology employed herein is for the purpose of description and not of limitation. The means and materials for carrying out various disclosed functions may take a variety of alternative forms without departing from the invention.

Thus, the expressions "means to . . . " and "means for . . . " as may be found in the specification above and/or in the claims below, followed by a functional statement, are intended to define and cover whatever structural, physical, chemical, or electrical element or structures which may now or in the future exist for carrying out the recited function, whether or nor precisely equivalent to the embodiment or embodiments disclosed in the specification above. It is intended that such expressions be given their broadest interpretation.

What is claimed is:

1. A mask covering at least the nose and mouth of a wearer, said mask consisting essentially of filtering media for filtering air to the wearer;

said mask having an area approximately over the mouth of the wearer that can be opened and closed at will without removing the mask;

said area selected from the group consisting of:

a. an opening covered by elastic or flexible material;

b. elastic or flexible material that is self-closing;

c. an elastic or flexible flap over a hole or aperture;

d. a detachable flexible or elastic patch over a hole or aperture; and e. an aperture or hole which is self-opening and self-closing, said area being constructed such that said area opens when a device is inserted into the area and closes when the device is removed therefrom.

2. The mask according to claim 1 wherein the area that can be opened or closed at will comprises a hole or aperture covered with touching or overlapping pieces of elastic or flexible material.

3. The mask according to claim 1 wherein the area that can be opened and closed at will comprises a hole or aperture covered with a flap made of elastic or flexible material attached to the mask.

4. The mask according to claim 1 wherein the area that can be opened and closed at will is formed of an elastic or flexible self-closing material over a hole or aperture.

5. The mask according to claim 1 further comprising attachments to maintain the mask in place on a wearer.

6. The mask according to claim 1 wherein the area that can be opened and closed at will comprises a hole or aperture which is covered by a flexible or elastic removable patch which can be re-affixed to the mask.

7. The mask according to claim 1 which substantially covers the wearer's head.

8. The mask according to claim 1 which is made of a flexible material.

9. The mask according to claim 1 wherein said area approximately over the mouth of the wearer is self-closing.

* * * * *

UNITED STATES PATENT AND TRADEMARK OFFICE

CERTIFICATE OF CORRECTION

PATENT NO. : 7,044,127 B1

APPLICATION NO. : 10/659325

DATED : May 16, 2006

INVENTOR(S) : Fernandez DeCastro

It is certified that error appears in the above-identified patent and that said Letters Patent is hereby corrected as shown below:

1) On the Title page, in item 76, in the inventor's name, delete "P.O." and insert therefor --PhD--.

2) On the Title page, in item 76, in the inventor's address, delete "Box 1984" and insert therefor --P.O. Box 1824--.

Signed and Sealed this

Twelfth Day of December, 2006

JON W. DUDAS

*Director of the United States Patent and Trademark Office*